US00PP17667P2

(12) United States Plant Patent
Trees

(10) Patent No.: US PP17,667 P2
(45) Date of Patent: Apr. 24, 2007

(54) ***GERANIUM* PLANT NAMED 'BALDESIMRED'**

(50) Latin Name: *Pelargonium×hortorum*
Varietal Denomination: Baldesmired

(75) Inventor: Scott C. Trees, Shell Beach, CA (US)

(73) Assignee: Ball Horticultural Company, West Chicago, IL (US)

( * ) Notice: Subject to any disclaimer, the term of this patent is extended or adjusted under 35 U.S.C. 154(b) by 0 days.

(21) Appl. No.: 11/272,537

(22) Filed: Nov. 10, 2005

(51) Int. Cl.
*A01H 5/00* (2006.01)

(52) U.S. Cl. ..... Plt./330
(58) Field of Classification Search ..... Plt./330
See application file for complete search history.

*Primary Examiner*—Kent Bell
*Assistant Examiner*—June Hwu
(74) *Attorney, Agent, or Firm*—Audrey Charles

(57) ABSTRACT

A new and distinct cultivar of *Geranium* plant named 'Baldesimred' characterized by its semi-double medium red-colored flowers, medium green-colored foliage with a faint, slightly darker green-colored zone, and moderately vigorous, upright growth habit.

1 Drawing Sheet

Latin name of genus and species of plant claimed: *Pelargonium×hortorum.*
Variety denomination: 'Baldesimred'.

BACKGROUND OF THE INVENTION

The present invention relates to a new and distinct cultivar of *Geranium* plant botanically known as *Pelargonium× hortorum* and hereinafter referred to by the cultivar name 'Baldesimred'.

The new cultivar originated in a controlled breeding program in Arroyo Grande, Calif. during January 2002. The objective of the breeding program was the development of *Geranium* cultivars that flower uniformly, have attractive flower and foliage colors, and a medium vigorous and upright growth habit.

The female (seed) parent of the new cultivar was 'Americana Dark Red', U.S. Plant Pat. No. 9,307, characterized by its semi-double dark red-colored flowers, large umbels, medium green-colored foliage with faint zonation, and vigorous growth habit. The male (pollen) parent of the new cultivar was 'Fip 553', U.S. Plant Pat. No. 13,961, characterized by its semi-double deep red-colored flowers, large, full umbels, and vigorous, well branched growth habit. The new *Geranium* was discovered and selected by the inventor as a single flowering plant within the progeny of the above stated cross-pollination during May 2002 in a controlled environment at Arroyo Grande, Calif.

Asexual reproduction of the new cultivar by terminal stem cuttings since May 2002 at Arroyo Grande, Calif. and West Chicago, Ill. has demonstrated that the new cultivar reproduces true to type with all characteristics, as herein described, firmly fixed and retained through successive generations of such asexual propagation.

SUMMARY OF THE INVENTION

The following characteristics of the new cultivar have been repeatedly observed and can be used to distinguish 'Baldesimred' as a new and distinct cultivar of *Geranium* plant:

1. Semi-double, medium red-colored flowers;
2. Medium green-colored foliage with a faint, slightly darker green-colored zone; and
3. Moderately vigorous and upright growth habit.

Plants of the new cultivar differ from plants of the female parent primarily in flower color and growth habit and from plants of the male parent primarily in flower color and growth habit.

Of the many commercially available *Geranium* cultivars known to the inventor, the most similar in comparison to the new cultivar is 'BFP-1328 Red', U.S. Plant Pat. No. 10,399. However, in side-by-side comparisons, plants of the new cultivar differ from plants of 'BFP-1328 Red' in the following characteristics:

1. Plants of the new cultivar have less foliage zonation than plants of 'BFP-1328 Red'; and
2. Plants of the new cultivar have a slightly different flower color from plants of 'BFP-1328 Red'.

BRIEF DESCRIPTION OF THE PHOTOGRAPHS

The accompanying photographs show, as nearly true as it is reasonably possible to make the same in color illustrations of this type, typical flower and foliage characteristics of the new cultivar. Colors in the photographs differ slightly from the color values cited in the detailed description, which accurately describes the colors of 'Baldesimred'. The plants were grown in 10 cm pots for 10 weeks in a greenhouse at West Chicago, Ill.

DETAILED BOTANICAL DESCRIPTION

Figure 1:
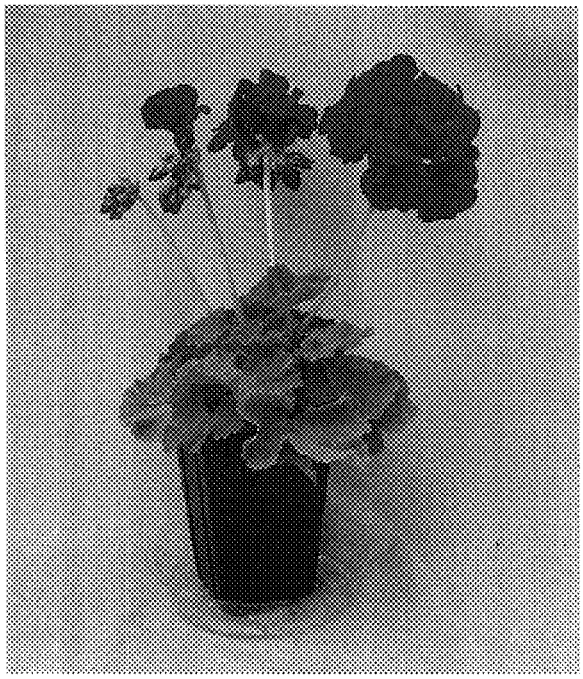
FIG. 1 illustrates a side view of the overall growth and flowering habit of 'Baldesimred'.
Figure 2:
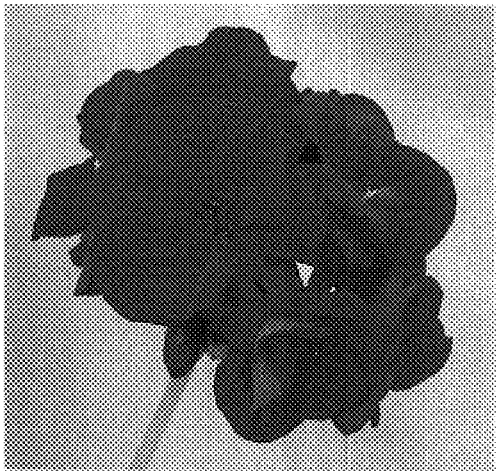
FIG. 2 illustrates a close-up view of a single umbel of 'Baldesimred'.
Figure 3:
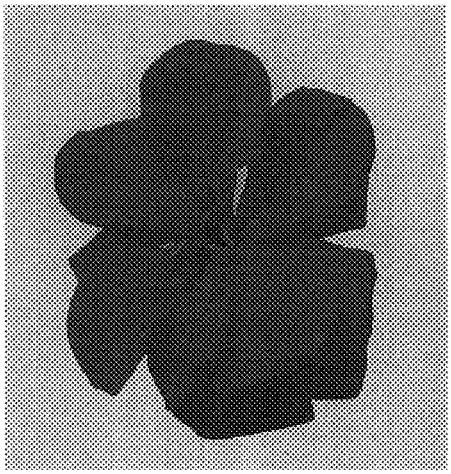
FIG. 3 illustrates a close-up view of a single floret of 'Baldesimred'.

The new cultivar has not been observed under all possible environmental conditions to date. Accordingly, it is possible that the phenotype may vary somewhat with variations in the environment, such as temperature, light intensity, and day length, without, however, any variance in genotype.

The chart used in the identification of colors described herein is The R.H.S. Colour Chart of The Royal Horticultural Society, London, England, 2001 edition, except where general color terms of ordinary significance are used. The color values were determined on May 23, 2005 between 3:00 p.m. and 4:00 p.m. under natural light conditions, in West Chicago, Ill.

The following descriptions and measurements describe plants produced from cuttings taken from stock plants and grown in a double polycarbonate-covered greenhouse under conditions comparable to those used in commercial practice. The plants were grown at West Chicago, Ill. in 10 cm pots for 10 weeks utilizing a soilless growth medium. Greenhouse temperatures were maintained at approximately 65° F. to 75° F. (18° C. to 24° C.) during the day and approximately 62° F. to 68° F. (17° C. to 20° C.) during the night. Greenhouse light levels of 3,500 to 6,000 footcandles were maintained during the day.

Botanical classification: *Pelargonium×hortorum* cultivar 'Baldesimred'.

Parentage:

*Female parent.*—'Americana Dark Red', U.S. Plant Pat. No. 9,307.

*Male parent.*—'Fip 553', U.S. Plant Pat. No. 13,961.

Propagation:

*Type cutting.*—Terminal stem.

*Time to initiate roots.*—Approximately 10 to 14 days.

*Time to produce a rooted cutting.*—Approximately 21 to 28 days.

*Root description.*—Fibrous.

*Rooting habit.*—Freely branching.

Plant description:

*Crop time.*—Approximately 8 to 9 weeks from a rooted cutting.

*Growth habit and general appearance.*—Moderately vigorous and upright.

*Size.*—Height from soil level to top of plant plane: Approximately 23.1 cm. Height from soil level to top of foliage: Approximately 11.6 cm. Width: Approximately 27.1 cm.

*Branching habit.*—Freely basal branching. Approximately 4 branches per plant.

*Branch.*—Strength: Strong. Length: Approximately 4.1 cm. Diameter: Approximately 7.7 mm. Texture: Densely pubescent with short, soft hairs. Color: 144B. Internode length at center of branch: Approximately 1.3 cm.

*Foliage.*—Number of leaves per lateral branch: Approximately 10. Fragrance: None. Form: Simple. Arrangement: Opposite. Aspect: Petiole is at acute angle to stem and blade is at a right angle to stem. Shape: Reniform. Margin: Crenate. Apex: Obtuse. Base: Cordate. Venation pattern: Palmate. Length of mature leaf: Approximately 4.5 cm. Width of mature leaf: Approximately 7.2 cm. Texture of upper and lower surfaces: Densely pubescent with short, soft hairs. Color of upper surface of mature foliage: 137A with venation of 145B and a faint zone slightly darker than 137A around the outer half of leaf. Color of lower surface of mature foliage: 137C with venation of 145B. Petiole length: Approximately 5.0 cm. Petiole diameter: Approximately 2.2 mm. Petiole texture: Densely pubescent with short, soft hairs on both upper and lower surfaces. Petiole color: Darker than 144A.

Flowering description:

*Flowering habit.*—'Baldesimred' is freely flowering under outdoor growing conditions with substantially continuous blooming from spring through autumn and year round in greenhouse environment.

*Time to first flower.*—Approximately 9.5 weeks from sticking of unrooted cutting.

*Lastingness of individual floret.*—Approximately 5 to 7 days.

Inflorescence description:

*Type.*—Umbel. Position: Above foliage. Number of open umbels at ten weeks: Approximately 2. Number of developing umbels at ten weeks: Approximately 3. Umbel diameter: Approximately 9.2 cm. Umbel height/depth: Approximately 6.7 cm. Number of flowers per umbel: Approximately 10. Fragrance: None.

*Peduncle.*—Strength: Strong. Aspect: Acute angle to stem. Length: Approximately 15.3 cm. Diameter: Approximately 3.9 mm. Texture: Densely pubescent with short, soft hairs. Color: 144A.

Flower description:

*Bud rate of opening.*—Generally takes 3 to 5 days for bud to progress from first color to fully open flower.

*Bud just before opening.*—Shape: Elliptic. Length: Approximately 1.5 cm. Diameter: Approximately 9.2 mm. Petal color: Closest to 43A. Texture: Villous.

*Corolla.*—Form: Semi-double. Shape: Round. Diameter: Approximately 5.4 cm. Depth: Approximately 1.7 cm.

*Petals/petaloids.*—Quantity: Approximately 7 petals and 2 to 3 irregular shaped petaloids per flower. Appearance: Iridescent. Aspect: Cupped. Arrangement: Imbricate. Shape: Obovate. Apex: Obtuse. Base: Attenuate. Margin: Entire. Texture of upper and lower surfaces: Glabrous. Length of upper petal: Approximately 3.0 cm. Width of upper petal: Approximately 2.4 cm. Length of lower petal: Approximately 2.8 cm. Width of lower petal: 2.9 cm. Color of upper surface of upper petal: Closest to 43A with venation from base to center of 53A. Color of lower surface of upper petal: Closest to 43B with venation from base to center of 53B. Color of upper surface of lower petal: Closest to 45A with venation of 45A. Color of lower surface of lower petal: Closest to 43B with venation of 43A.

*Pedicel.*—Strength: Strong. Angle: Acute. Length: Approximately 2.8 cm. Diameter: Approximately 1.3 mm. Texture: Densely pubescent with short, soft hairs. Color: 145A with overlay of 183B.

*Calyx.*—Shape: Five-pointed star. Width: Approximately 2.0 cm.

*Sepals.*—Quantity per floret: 5. Shape: Lanceolate. Apex: Acuminate. Margin: Entire. Length of upper sepal: Approximately 1.2 cm. Width of upper sepal: Approximately 4.2 mm. Length of lower sepal: Approximately 1.2 cm. Width of lower sepal width: Approximately 2.9 mm. Texture of upper surface: Glabrous. Texture of lower surface: Villous. Color of upper and lower surfaces: 143B with venation of 46A.

*Reproductive organs.*—Androecium: Quantity of mature anthers: Approximately 8 per flower. Anther shape: Oblong. Anther length: Approximately 2.0 mm. Anther color: 67A. Pollen amount: Abundant. Pollen color 163A. Gynoecium: Pistil quantity: One per floret. Pistil length: Approximately 1.2 cm. Stigma shape: Five branched. Stigma length: Approximately 3.1 mm. Stigma color: 53B. Style length: Approximately 2.3 mm. Style color: 53C. Ovary length: Approximately 6.1 mm. Ovary texture: Sericeous. Ovary color: 144B.

Seed and fruit production: Neither seed nor fruit production has been observed.

Disease and pest resistance: Resistance to pathogens and pests common to *Geranium* has not been observed.

What is claimed is:

1. A new and distinct cultivar of *Geranium* plant named 'Baldesimred', substantially as herein shown and described.

* * * * *